United States Patent
Winger et al.

(10) Patent No.: US 10,444,076 B2
(45) Date of Patent: Oct. 15, 2019

(54) INFRARED DEVICE

(71) Applicant: Sensirion AG, Stafa (CH)

(72) Inventors: Martin Winger, Stafa (CH); Marc Von Waldkirch, Stafa (CH); Matthias Streiff, Stafa (CH); Alexander Lochbaum, Zurich (CH); Jürg Leuthold, Zurich (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 15/778,753

(22) PCT Filed: Nov. 26, 2015

(86) PCT No.: PCT/CH2015/000172
§ 371 (c)(1),
(2) Date: May 24, 2018

(87) PCT Pub. No.: WO2017/088071
PCT Pub. Date: Jun. 1, 2017

(65) Prior Publication Data
US 2018/0356290 A1    Dec. 13, 2018

(51) Int. Cl.
*G01J 5/08* (2006.01)
*G01J 3/427* (2006.01)
(Continued)

(52) U.S. Cl.
CPC ............... *G01J 5/0853* (2013.01); *G01J 3/42* (2013.01); *G01J 3/427* (2013.01); *G01J 5/061* (2013.01);
(Continued)

(58) Field of Classification Search
CPC ............... G01N 21/3563; G01N 30/88; G01N 35/00732; G01N 33/497; G01N 21/3504;
(Continued)

(56) References Cited

U.S. PATENT DOCUMENTS 8,618,481 B2 * 12/2013 Nikoobakht .......... B81B 3/0081
250/338.1
9,006,857 B1 * 4/2015 Carr .................. H01L 27/14601
257/12
(Continued)

FOREIGN PATENT DOCUMENTS

EP    2732253    5/2014

OTHER PUBLICATIONS

PCT International Search Report No. PCT/CH2015/000172, dated Aug. 3, 2016, completed on Jul. 15, 2016.
(Continued)

*Primary Examiner* — Taeho Jo
(74) *Attorney, Agent, or Firm* — Cooper & Dunham LLP (57) ABSTRACT

An infrared device comprises a substrate (1), and arranged on or in the substrate (1) a configuration (3) for one of selectively emitting and selectively absorbing infrared radiation of a band, the configuration (3) comprising a pattern made from an electrically conducting material on a first level (L1), an electrically conducting film (33) on a second level (L2), and a dielectric layer (24) between the pattern and the film (33). One or more of a heater (4) for heating the configuration (3), and a thermal sensor (5) arranged for sensing the selective infrared radiation of the band absorbed by the configuration (3) on or in the substrate.

20 Claims, 4 Drawing Sheets

(51) Int. Cl.
*G01J 5/06* (2006.01)
*G01J 5/10* (2006.01)
*G01N 21/3504* (2014.01)
*G01J 3/42* (2006.01)

(52) U.S. Cl.
CPC ............ *G01J 5/10* (2013.01); *G01N 21/3504* (2013.01); *G01J 2005/106* (2013.01)

(58) Field of Classification Search
CPC .... G01J 5/023; G01J 5/0853; G01J 2005/123; G01J 5/02; G01J 5/024; G01J 5/045; G01J 5/06; G01J 5/08; G01J 5/0837; G01J 5/12; G01J 5/14; G01J 3/42; G01J 3/427; G01J 5/061; G01J 5/10; G01J 2005/106
USPC .................................................... 250/339.02
See application file for complete search history.

(56) References Cited

U.S. PATENT DOCUMENTS

| | | | | |
|---|---|---|---|---|
| 2003/0060034 A1* | 3/2003 | Beyne | ................ | H01L 21/6835 438/618 |
| 2007/0048180 A1* | 3/2007 | Gabriel | ................. | B82Y 15/00 422/400 |
| 2007/0171120 A1* | 7/2007 | Puscasu | ................. | G01J 3/108 342/53 |
| 2008/0220535 A1* | 9/2008 | LeBoeuf | ................ | B82Y 30/00 436/164 |
| 2009/0207226 A1* | 8/2009 | Ikeda | .................... | B41J 2/0057 347/103 |
| 2010/0213373 A1* | 8/2010 | Meinel | ..................... | G01J 5/12 250/338.4 |
| 2012/0235067 A1* | 9/2012 | Araci | .................... | B82Y 20/00 250/504 R |
| 2012/0298867 A1* | 11/2012 | Nishikawa | ............ | G01J 5/0014 250/338.3 |
| 2012/0322164 A1* | 12/2012 | Lal | ......................... | B82Y 10/00 436/501 |
| 2013/0186178 A1* | 7/2013 | Usagawa | .................... | B82Y 15/00 73/31.06 |
| 2014/0111844 A1* | 4/2014 | Puscasu | ............. | H01Q 15/0066 359/245 |
| 2014/0131577 A1* | 5/2014 | Meinel | ..................... | G01J 5/12 250/338.4 |
| 2014/0175585 A1* | 6/2014 | Iguchi | .................. | H01L 31/184 257/431 |
| 2014/0260546 A1* | 9/2014 | Chen | .................... | G01N 27/128 73/31.06 |
| 2014/0291704 A1* | 10/2014 | Ali | ........................... | H01L 33/34 257/88 |
| 2015/0033827 A1* | 2/2015 | Burgi | .................... | G01N 27/04 73/31.06 |
| 2015/0276489 A1* | 10/2015 | Cumming | ............ | G01J 5/0881 250/338.3 |
| 2017/0363589 A1* | 12/2017 | Kumar | ................... | G01N 25/18 |

OTHER PUBLICATIONS

H.T. Miyazaki et al., Chemphyschem Articles, "Dual-band Infrared Metasurface Thermal Emitter for Co2 Sensing", Applied Physics Letters AIP Publishing LLC, vol. 105, No. 12, Sep. 22, 2014.

Kai Chen et al., "Dual-Band Perfect Absorber for Multispectral Plasmon-Enhanced Infrared Sepctroscopy", ACS Nano, vol. 6, No. 9, Sep. 25, 2012, pp. 7998-8006.

Katsuya Masuno et al., "Multiwavelength Selective IR Emission Using Surface Plasmon Polaritons for Gas Sensing" IEE Photonics Technology Letters, vol. 23, No. 22, Nov. 1, 2011, pp. 1661-1663.

* cited by examiner

INFRARED DEVICE

CROSS REFERENCE TO RELATED APPLICATIONS

This application is a § 371 national stage of PCT International Application No. PCT/CH2015/000172, filed Nov. 26, 2015, which is incorporated herein in its entirety by this reference.

TECHNICAL FIELD

The present invention relates to an infrared device, an infrared emitter comprising such infrared device, an infrared detector comprising such infrared device, and to an infrared based sensor containing such infrared devices.

BACKGROUND ART

Conventional gas sensors based on infrared radiation are big in size and hence not suited for integration into mobile electronics, for example. Hence, it is desired to provide a small-scale infrared device that can inter alia be used in gas sensing applications.

DISCLOSURE OF THE INVENTION

According to an aspect of the present invention, an infrared device is provided comprising a substrate. A configuration is supported by the substrate, i.e. arranged on or in the substrate. The configuration is adapted to selectively emit or selectively absorb infrared radiation of a frequency or wavelength band, which preferably is a defined band which is rather narrow. In case the configuration is heated by a heater, the configuration emits infrared radiation in the defined band. In case the configuration is exposed to e.g. broad band infrared radiation, only the infrared radiation in the defined band is absorbed by the configuration and converted into heat sensed by a thermal sensor. For example, the infrared radiation incident on the configuration may be a broadband infrared radiation. However, it may be desired to detect and quantify an infrared radiation of a given frequency band within the broadband only, which is supported by the configuration selectively absorbing infrared radiation, i.e. solely in the subject band but near to zero absorption outside this wavelength band. Such band limited infrared absorption may serve as a basis for e.g. determining the presence of a gas compound in the environment of the device which gas compound e.g. may specifically absorb infrared radiation in the subject band.

The band may be as narrow as to contain a single frequency only, but in practice may rather encompass a frequency range, preferably a frequency range around a center frequency of interest, which band may e.g. have Gaussian-like or Lorentzian-like characteristic around the center frequency. In this respect and in particular for a detector the configuration may act as a filter for filtering the infrared frequencies of the subject band out of a broader band. In case of an emitter, the configuration generates and emits infrared frequencies only in the subject band. As a result, infrared radiation only of the filtered band is emitted from or absorbed by the configuration for further processing. Hence, in case of an emitter, a device is suggested providing infrared emission in a narrow band which in turn may be beneficial in powering the device and in enhancing the spectral flux in the subject band per power unit supplied. In case of the device being designed as a detector, background noise from frequencies outside the band can be reduced or eliminated by selective absorption in the band only. Hence, by means of the present device, an emissive or receptive spectrum of infrared radiation can be shaped to a desired band. The suggested device therefore is considered as wavelength selective in a range of wavelengths corresponding to the desired band, and hence either as a wavelength selective emitter or a wavelength selective detector. The present device preferably can be used in gas sensing, spectroscopy, infrared imaging and/or signaling applications without limitation.

As indicated above, the configuration may work in two different ways subject to elements supported by the substrate:

In case a heater is added, the heat generated may be conducted by intermediate structures, e.g. layers on the substrate or the substrate itself, to the configuration. In response to the configuration being exposed to this heat the configuration emits infrared radiation only in the subject band. In such case, the infrared device acts as an infrared emitter—in short emitter—for emitting infrared radiation in the defined band only, but not outside the band. Here, the power source causing infrared radiation of the defined band to be emitted is the heater of the device and a destination for the emitted infrared radiation is outside the device. In a different variant, the configuration is exposed to broadband infrared radiation from the outside and selectively absorbs infrared radiation in the desired band only. In this case, the absorbed infrared radiation of the defined band is converted into heat by the configuration which heat is sensed by a thermal sensor and converted into an electrical signal, a magnitude of which signal may be proportional to the intensity of the radiation in the subject band. In this variant, the infrared device acts as an infrared detector—in short detector—for detecting and converting the selectively absorbed infrared radiation from the configuration. While the origin of the broadband infrared radiation is outside the device, a destination for the absorbed portion of infrared radiation in the defined band is the thermal sensor.

By means of the substrate supporting the heater or the thermal sensor as well as the configuration, a small-scale device can be manufactured. Preferably, all of the elements heater, thermal sensor and configuration are arranged and/or integrated on or in the substrate, directly or indirectly, in a non-removable fashion. Such close arrangement may decrease power required to operate the infrared emitter and/or lower responsivity required to generate a signal of sufficient magnitude in the thermal sensor which in turn may reduce size of the device itself or the thermal sensor included in such a device.

The substrate preferably is a semiconductor substrate such as a silicon substrate, but in different embodiments the substrate may be a ceramic substrate or a substrate of a different material. An arrangement of the configuration on the substrate includes an arrangement directly on a surface of the substrate, or indirectly on any intermediate layer deposited on the substrate. Hence, it suffices that the substrate supports the configuration.

In a preferred embodiment a recess is provided in the substrate, and a membrane spans at least a portion of the recess in the substrate. In such embodiment, it is preferred that the configuration is arranged on or in the membrane, and preferably is limited to the arrangement on or in the membrane. In case the film is a continuous film facing all elements of the pattern, it is preferred that the film is limited in its extension to the area of the membrane. The recess is manufactured into the substrate by means of etching or otherwise removing material. The recess may go through the entire substrate and as such open the substrate from a backside thereof, while at a front side of the substrate opposite the backside a membrane is arranged spanning at least a portion of the recess. In a different embodiment, the recess does not lead through the entire substrate but forms a cavity in the front side of the substrate that at least is partially spanned by the membrane. In one embodiment, the membrane completely covers the recess without an exchange of gas through the membrane from the recess to the outside or vice versa. In a different variant, the membrane may contain holes for allowing such exchange. The membrane may also take the shape of a bridge bridging the recess and allowing gas to be exchanged between the recess and a volume outside the membrane. In such embodiment, a thermal mass of the membrane may even be reduced compared to a continuous membrane resulting in an improved thermal insulation which in turn improves response time and responsivity, and makes the device more energy efficient. A bridge-shaped membrane may be applied to an emitter device, and/or to a detector device. The membrane may be formed from a material applied to the front side of the substrate. Such material may include a layer stack which may contain dielectric layers and metal layers, preferably alternating, and preferably such as used in CMOS processing. Once substrate material is removed, e.g. from the backside of the substrate, a membrane may remain e.g. made from all or at least some layers of the stack, or made from all the layers of the stack and additionally from a portion of the substrate.

The heater, if any, preferably is arranged on or in the membrane, if any, too, and as such may heat the configuration. High temperatures can be achieved in the membrane by low power owed to the small dimension of the membrane. Heat generated by the heater is conducted to the configuration efficiently and swift preferably by thermal conductive structures. At the same time, a thermal conduction along the thin membrane is sufficiently small not to induce high temperatures in the rest of the semiconductor chip, which otherwise would impact any electronic circuitry which in one embodiment may be integrated in the substrate, e.g. by CMOS processing. The vast difference of thermal masses of membrane and substrate in addition ensure that the substrate may to a large extent remain at room temperature. Such electronic circuitry may be integrated for one or more of controlling the heater and/or for processing signals from the thermal sensor in form of a determination unit as will be explained later on.

A thermal sensor, if any, may be arranged on or in the membrane, too, e.g. in case the thermal sensor includes one or more thermocouples that may be placed such that hot junctions thereof are arranged on or in the membrane, and cold junctions thereof are arranged outside the membrane on the substrate for allowing to detect a difference in temperature. In a different embodiment, a temperature sensor is provided based on measuring a resistance change. An example for such a resistive temperature sensor is a bolometer that preferably comprises a resistive temperature sensor made from conductive structures such as metal wires arranged in the stack, and preferably in or on the membrane if any. A thermal mass of the bolometer is represented by the configuration.

A good thermal isolation is achieved, in case the configuration and the thermocouples or the resistive temperature sensor is arranged on or in a membrane. In such embodiment, an additional temperature sensor in from of a resistive wire or a thermocouple may be provided and arranged on or in the membrane for monitoring a temperature thereof. Preferably, the measured temperature is used for controlling a temperature of the membrane e.g. by a heater. By such means, it could be compensated for drifts induced by degradation of the heater if any during operation.

The configuration comprises a pattern on a first level made from an electrically conducting material, an electrically conducting film on a second level, and a dielectric layer between the pattern and the film. The first and the second level may denote planes in parallel to a planar extension of the substrate, or in parallel to the membrane, if any.

In case a stack of layers is provided on the substrate, such as insulating and conductive layers arranged on a top surface of the substrate in alternating fashion, the set of elements and the film are preferably made from two different conductive layers of the stack, and the dielectric layer is made from a dielectric layer of the stack. In case of a membrane being formed by the layer stack, the configuration may be formed from the respective layers in the portion of the stack spanning the recess, which is the membrane. A conductive layer may e.g. be a metal layer. The stack may additionally include semiconducting layers.

Preferably, the heater, if any, is made from a metal layer of the stack that is different to the metal layers the pattern and the film are made from. In one embodiment, the film at the same time may represent the heater, and hence, the heater and the film may be made from the same metal layer.

Preferably, the at least one thermocouple, or a thermopile comprising multiple thermocouples, may be made from conducting or semiconducting layers of the stack, too, that preferably are different to the conducting layers the pattern and the film are made from.

The configuration can in one embodiment be considered as a metamaterial perfect absorber (MPA), wherein the metamaterial property denotes an artificially behaving electromagnetic material that evokes an electromagnetic response typically not available in nature. Given that according to Kirchhoff's thermal law, the emissivity of the subject configuration equals its absorptivity, such that the configuration can be used for building both, an emitter and a detector. By designing the configuration appropriate, the emissivity and the absorptivity of the MPA can be tailored to the desired band/wavelengths. In response to incident heat or electromagnetic waves, and specifically in response to incident heat or infrared radiation, the configuration resonates at a frequency that is proportional to the dimension of at least one of the extensions of an element contributing to the pattern. In turn, the dimensioning of the pattern, and specifically the dimensioning of such element extension can be selected such that the configuration resonates in the desired band/wavelength. In this context, the configuration couples to electric and magnetic components of the incident radiation or to heat applied to the configuration. Reflectance of the configuration preferably is minimized in the subject band, e.g. by setting an impedance of the configuration to the impedance of free space, and transmission is reduced in the configuration e.g. by making the film having a thickness that preferably exceeds a penetration depth of incident infrared radiation. For the infrared domain, it is preferred that the thickness of the film is at least 50 nm. Overall, the configuration may become an emitter or absorber for the desired band only. Heat or an incident infrared radiation is believed to generate antiparallel currents in the element and the film resulting in the resonance response. Preferably, a thickness of the dielectric layer between the film and each of the elements is less than the center wavelength of the band, and in a preferred embodiment is less than 500 nm. A thickness of the element of the metallic layer preferably is less than the center wavelength, too, and in a preferred embodiment is less than 500 nm. Given that a light—material interaction is evoked, the result can be described as polariton. However, in contrast to plasmon surface polaritons described in the art, the present device preferably does not make use of plasmon surface polaritons which may be generated by a pattern of metallic elements only without the requirement of an additional dielectric layer—metallic film stack. Instead, a property of magnetic polaritons is used which is a resonance invoked by the pattern—film combination rather than a bare surface effect on the metallic—air interface. Hence, in a preferred embodiment, the magnetic polariton is considered as dominant effect to be exploited, while the plasmon surface polariton may arise at the same time, but will not be exploited.

Preferably, the pattern of the configuration may comprise a set of electrically conducting, and preferably metallic elements, also referred to as first elements in the following, e.g. made from Al, Cu, W, Pt, or Au disconnected from each other by gaps. The gaps may or may not be filled by dielectric material. Hence, individual elements disconnected from each other and each made from an electrically conducting material may contribute to the pattern in this embodiment. The elements of the pattern may be spread over the entire area available on the substrate, or only over a portion thereof, or over a membrane if any, or over a portion of such membrane. A dense pattern is preferred in order to achieve maximum absorptivity/emissivity. In this setting, "dense" means dense on the length scale of wavelength: Once there is more than one element per area of the size of a wavelength square, the emissivity/absorptivity is expected to "saturate" at a maximum level.

Preferably, the elements are made from a common layer of conducting material, such as a metal layer of a CMOS layer stack, which is structured accordingly, e.g. by conventional microfabrication processes. The elements of the set may reside on the dielectric layer of the configuration, which dielectric layer may represent an insulating layer of the layer stack, such as a CMOS layer stack, e.g. made from $SiO_2$ or SiN. In a different embodiment, the elements of the set may be embedded in dielectric material, as long as a dielectric layer is arranged between each of the elements of the set and the film, which means that the elements and the film are not electrically connected. An area in the first level in between two neighboring elements of the set is defined as gap. Hence, a gap may be defined as area not covered by the conducting material in the first level between two elements.

In a different embodiment, an electrically conducting layer in the first level, such as a metal layer preferably made from one of the materials introduced above comprises gaps in form of holes which collectively define the pattern. In this embodiment, the portion of the conducting layer between two neighboring holes may be considered as element of the set given that such element is limited in its extension at least in one direction by the neighboring gaps. Hence, such element has a characteristic extension, too, although it may be connected to other virtual elements of the layer between two other holes. In this regard, it is legitimate to virtually separate the conducting layer being a continuous layer except for the holes in virtual adjacent (and connected) elements serving the same purpose as the separated elements addressed in the previous embodiment.

In particular when the elements are disconnected, the device may comprise exclusively identical elements, or may comprise elements different in shape, e.g. elements of two different shapes. Hence, a device may in one embodiment comprise a set of first elements, and a set of second elements different in one of shape and size from the first elements. In one embodiment, a first and a second element may be connected to an element pair which element pairs are disconnected from each other. The number of elements in a set—be it the set of first elements or the set of second elements if any—may be at least one, but preferably is two or more, and preferably is more than 50. The allocation of elements of the one or more sets on the dielectric layer may result in the pattern. In case of different elements, e.g. first and second elements, these elements may be arranged intermingled, in particular when the device is embodied as an emitter. As described above, the pattern preferably extends in a plane parallel to the membrane, on the first level.

The dielectric layer between the film and the pattern preferably is a continuous dielectric film also extending underneath gaps in the pattern. In a different embodiment, the dielectric layer may at least extend between the pattern and the film, but not underneath the gaps in the pattern. The film preferably is a continuous metallic film. In a different embodiment, the film only extends in areas that are defined by a projection of the pattern and gaps in the pattern onto the second level. In case the gaps are restricted to gaps of neighboring elements of the pattern, the film may contain some gaps in itself. In a different embodiment, the metallic film extends in an area of at least 80 percent of an area defined by a circumference around the pattern as a whole.

An element of the set preferably is characterized by an extension in the very first level which extension is dimensioned as significant for impacting and specifically for controlling the emission of infrared radiation in the desired band only. This extension of the element is dimensioned such that in combination with the film a selective emission or absorption of infrared radiation in the desired band is achieved. For this purpose, it is preferred that the subject extension of the element is dimensioned to be a quarter of the wavelength that corresponds to the center frequency of the desired band. It is understood, that the dimensioning of a quarter of the wavelength shall include a tolerance of at maximum+/−20 percent. The frequency f and the wavelength $\lambda$ are related by $f=c/\lambda$, wherein c is the speed of light. Hence, for example in case the wavelength $\lambda=4.3$ μm which is a wavelength known to be absorbed by $CO_2$ defines the band for emissivity and absorptivity, the extension me/ue of the one or more elements is determined by me/ue=4.3 μm/4=1.075 μm. The configuration is then adapted to selectively emit infrared radiation of this wavelength/band to a gas potentially comprising $CO_2$ in case the device being an emitter, or to selectively absorb infrared radiation of this wavelength/band which may allow determining the absorption rate of $CO_2$ in a measurement volume containing gas. The absorption rate may be proportional to the concentration of $CO_2$ in the volume. Such determination can be achieved based on the known emitted radiant flux of the emitter in the subject band, and on the radiant flux in this band received at the thermal sensor. Of course, the emitter and/or detector, and specifically the corresponding configuration can also be tuned to determine the presence and/or concentration of other gas compounds, such as $N_2O$, CO, NO having absorption wavelengths $\lambda$ at 4.5 μm, 4.7 μm and 5.3 μm respectively.

The relevant extension may also be referred to as main extension in case the element shows different extensions in the relevant plane. In this case, the or any other extension of the element in the relevant plane is dimensioned very different from the main extension, e.g. is less than a third of the main extension, or less than a fifth. Hence, such subordinate extension of the element may also cause a selective emissivity or absorptivity of radiation at a band different from the desired band. This different band, however, may not be of relevance e.g. for the reason that such radiation is no longer in the infrared domain and therefore may not be detected by the thermal sensor of the associate detector, or may not be considered for other purposes: E.g. in case of an emitter if a temperature to which the configuration is heated by the heater is less than 500° C., no significant portions of visible radiation will be emitted. It is left to the choice of the designer dimensioning the elements to define the subordinate, i.e. the non-main extension of the elements such that any emission or absorption of radiation evoked by the non-main extension does not interfere with the purpose of the device. Specifically, the elements may extend mainly along a first axis, and to the subordinate extent along an axis orthogonal to the first axis in the plane. As a result, the elements may take the form of a stripe wherein a length of the stripe represents the main extension, and a width of the stripe represents the subordinate extension. It is not important, which axis within the first level is defined as first axis given that the resonating effect will be achieved irrespective of the orientation of the element in the first level. However, in case of multiple identical elements contributing to the set, it is preferred that the orientation of all elements of the set is the same in order to maximize the signal to noise ratio. And, an angular orientation of the elements in the first level has an influence on the polarization of emitted infrared light, in case of an emitter, or, on the polarization the absorber is sensitive to, in case of a detector. Hence, it is preferred that the main or uniform extension of elements show the same orientation in the emitter and detector in case of an arrangement comprising emitter and detector, for example.

In a different embodiment, the elements may not be designed to have a main extension and a subordinate extension, but may have a uniform extension along both orthogonal axis in the first level. Hence, such uniform extension represents the main extension of the element. Examples for a shape of such element are a circle, a square, or a cross with legs of the same length. In such cases, the diameter of e.g. the circle may be the uniform extension and as such the measure that defines the wavelength to be filtered, or the e.g. the length of the square, or e.g. the length of the legs of the cross.

In case the pattern contains only one kind of elements, such elements are also referred to as first elements, without the need to have different second elements. However, in a different embodiment, a set of second elements may be provided in the same configuration next to the set of first elements. Preferably, first and second elements then have a different main or uniform extension resulting in the configuration being selective to another, second band in the infrared spectrum in addition to the original, first band. Such other band corresponds to infrared radiation of a wavelength $\lambda_o$ different to the wavelength $\lambda$ of the band adjusted by dimensioning the extension of the first elements.

In case of multiple second elements, these second elements preferably are arranged in the same orientation. In case the second elements have a main extension, it is preferred that this main extension is oriented orthogonal to the main extension of the first elements. The definition of main and uniform extension shall apply to the second elements in the same way as to the first elements. Preferably, the second elements have the shape of a stripe each, however, with a length different, i.e. more or less than the length of the first element stripes. In case the second elements have a uniform extension, this uniform extension preferably is different to the uniform extension of the first elements. Preferably each second element takes the shape of one of a square, a circle and a cross in such case, and preferably, the second elements have the same shape as the first elements, however, have a different uniform extension, i.e. being different in one of length, diameter or span. It may be preferred that the second elements of a uniform extension are of the same orientation as the first elements.

In a preferred embodiment, the second elements are not only disconnected from each other, but are also disconnected from all of the first elements. However, in a different embodiment, the second elements are disconnected from each other, but each second element is connected with a first element forming an element pair. The element pairs again are disconnected from each other. In case the first and second elements both take the shape of a stripe, however of different length, the following shapes of a pair may be achieved:

A "T", an "L", a "†" or a "⊢" shape.

An element, be it a first or second element, can also take the shape of an ellipse, or a rectangle.

Preferably, in case of an arrangement including an emitter and a detector, the orientation of first elements in the detector and the orientation of second elements in the detector, which are preferably arranged orthogonal to each other, and which correspond to the orientation of the first and second elements in the emitter, provide for an additional separation of channels by polarization thereby avoiding crosstalk.

According to another aspect of the present invention, the infrared device according to any of the above embodiments is used and/or arranged as an infrared emitter, wherein the heater is included rather than the thermal sensor. As indicated above, the heater while being activated heats the configuration. In response to being heated, the configuration is excited to resonance in the desired band and selectively emits infrared radiation of the desired corresponding wavelength/s. This infrared radiation may then radiate into a volume filled by a gas to be measured. A gas component to be detected in the gas may specifically have the property to absorb infrared radiation of the defined wavelength/s that is emitted by the infrared emitter.

In a different aspect, an infrared emitter is proposed including a configuration with a set of first elements and a set of second elements different in one or more of shape and extension from the first elements. These different second elements are preferably arranged in the same configuration, preferably on or in the same membrane if any, preferably on or in different membranes spanning a common recess of the common substrate, and preferably on or in different membrane spanning different recesses in the common substrate.

Such infrared emitter is configured to selectively emit infrared radiation at two different bands. In particular in embodiments with the first and the second elements being arranged on or in the same membrane, a common heater may be used for heating all first and second elements. It is preferred to provide a common heater in order not to induce variations in the emissivity yet by using different heaters.

Hence, a surface of the infrared emitter can be structured with a periodic pattern which may contain multiple geometries that give rise to multiple emission peaks at different wavelengths. Similarly, when deployed on a thermal infrared detector, metamaterials with different absorption resonances give rise to spectrally selective detection.

According to a different aspect of the invention, an infrared device according to any of the above embodiments is used and/or arranged as an infrared detector, wherein the thermal sensor is included rather than the heater. As indicated above, the thermal sensor is exposed to heat stemming from the configuration which heat corresponds to the infrared radiation absorbed by the configuration in the desired band only. The configuration, however, may be exposed to broadband infrared radiation e.g. being received from a measuring volume that is in turn irradiated by an infrared heater, and preferably by an infrared heater of one of the previous embodiments. It is preferred in such scenario, that the configuration of the infrared emitter and the configuration of the infrared detector are identical such that the emitter selectively emits infrared radiation in the defined band into the measurement volume, and the detector selectively absorbs infrared radiation in the defined band, which is the portion of the selectively emitted radiation that is not absorbed by the gas compound to be detected.

In response to the exposure to this radiation stemming from the measuring volume, the configuration of the detector is excited to resonance in the desired band, absorbs infrared radiation of the selective defined wavelength, and converts the absorbed energy into heat supplied to the thermal sensor. The signal supplied by the thermal sensor may be evaluated by a determination unit and may indicate a concentration of the gas compound within the gas in the measuring volume.

Specifically, the thermal sensor comprises at least one thermocouple extending from the membrane of the detector to the substrate outside the recess. A hot junction of the different materials used for a thermocouple may be located on the membrane. In particular, a thermopile may be used comprising a multitude of connected thermocouples with all hot junctions residing on the membrane.

In a different embodiment, the thermal sensor includes a bolometer. A bolometer converts thermal radiation into a resistive measure, e.g. by means of a thermal mass absorbing the heat received and a temperature dependent electrical resistance thermally connected to the thermal mass. In a preferred embodiment, the bolometer presently comprises a resistive temperature sensor made from conductive structures such as metal wires arranged in the membrane. The thermal mass is represented by the configuration. A good thermal isolation is achieved, in case the configuration and the resistive temperature sensor are arranged on or in a membrane.

It is preferred, that the infrared device comprises an encapsulation for sealing a volume at one or both sides of the membrane or the substrate. The sealed volume may reduce the effect of heat conduction or convection to/from ambient air. The sealed volume may be evacuated or filled by a protective gas. Such encapsulation preferably includes a window for allowing the configuration to be exposed to the infrared radiation. The encapsulation can also be applied to a device including one or more thermocouples as thermal sensor, and to an infrared emitter.

In a different aspect of the present invention, an infrared detector is provided for detecting infrared radiation in two different bands. For this purpose, two of the infrared devices according to any of the previous embodiments are used and arranged, wherein it is preferred, that the configuration of the first infrared device is such that it contains only elements absorbing radiation of a desired band, and that the configuration of the second device is such that it contains only elements absorbing radiation of a different band referred to as other band. The elements of the first device preferably include first elements only but not any different elements, and the elements of the second device preferably include second elements only but not any different elements. The first device provides a first thermal sensor, while the second device provides a second thermal sensor different from the first thermal sensor, but preferably of the same kind, e.g. either both being based on thermocouple technology or both being based on bolometer technology.

The extension of each first element—be it a main extension or a uniform extension—is selected such that the first device absorbs radiation at the desired band, and the extension of each second element—be it a main extension or a uniform extension—is selected such that the second device absorbs radiation at the other desired different band, which typically requires a different extension. Accordingly, each first element of the first device is dimensioned to a wavelength $\lambda$ representing a center of the band divided by four, and each second element of the second device is dimensioned by a wavelength $\lambda_o$ representing a center of the other band divided by four. Hence, the configuration of the second infrared device is adapted for absorbing infrared radiation of a band different than the band of the first infrared device.

In view of the devices preferably including different thermal sensors, it is preferred that the substrates of the first and the second device are separate from each other, although the devices may be carried by a common carrier such as a leadframe, a land grid array or a PCB. However, in a different embodiment, the substrate of the first and the second device may be a common substrate, however, including two recesses, wherein the configuration of the first device is arranged on or in a membrane at least partly spanning the first recess, and the configuration of the second device is arranged on or in a membrane at least partly spanning the second recess. In case of the first and the second thermal sensor containing thermocouples, the thermocouples of both sensors may be arranged with a cold junction on the same substrate, however at different locations, and with the hot junctions on the different membranes. A bulk thermocouple may connect the different locations of the cold junctions in order to compensate for differing temperatures at these locations. In case of the first and the second thermal sensor containing bolometers, both of the bolometars may make use of the same encapsulation, e.g. of a common cap for sealing both the volumes next to the first and the second membrane of substrate at the same time.

Generally, an infrared detector may include more than two infrared devices, e.g. in case infrared radiation in more than two bands or corresponding wavelengths shall be detected. So may an infrared emitter.

According to another aspect of the present invention, an infrared based sensor is provided, comprising an infrared emitter according to any of the above embodiments, and an infrared detector according to any of the above embodiments. Such sensor may replace conventional $cm^2$ sized NDIR (Non-dispersive Infrared) sensors. The present infrared based sensor preferably is used as a gas sensor. In particular, it is preferred that the infrared based sensor includes an infrared emitter that is prepared for emitting infrared radiation at two different wavelengths, and a corresponding infrared detector configured to absorb infrared radiation at the very same two different wavelengths. By this means, a dual-channel infrared based sensor is designed comprising either two measurement channels or a measurement channel and a reference channel. In view of emitter and detector required to emit and absorb the same two bands, it is preferred that the configuration of the first device of the detector is adapted to selectively absorb infrared radiation of the same band that is selectively emitted by making use of the first elements of the configuration of the emitter. In the same way, the configuration of the second device of the detector is adapted to selectively absorb infrared radiation of the same other band that is selectively emitted by making use of the second elements of the configuration of the emitter. In terms of dimensioning the corresponding elements, it is preferred that the first elements of the emitter are identical to the first elements of the detector, i.e. the elements of the first device of the detector, and that the second elements of the emitter are identical to the second elements of the detector, i.e. the elements of the second device of the detector.

In such sensor, the first and second elements of the infrared emitter are arranged either on a common membrane, or on different membranes spanning a common recess in the common substrate. In a different embodiment, different substrates may be used for implementing the infrared emitter radiating at two different bands. The detector may be embodied on two different substrates, while in a different embodiment a common substrate may also be used containing two different recesses each of which at least partly being spanned by a membrane.

When the set-up of the infrared based sensor is chosen such that a measurement channel and a reference channel are provided, the band at which radiation is radiated by first elements of the emitter and at which radiation is absorbed by first elements of the detector corresponds to an absorption wavelength for a gas compound to be detected. In contrast, the other band at which radiation is radiated by the second elements of the emitter and at which radiation is absorbed by second elements of the detector corresponds to a wavelength not absorbed by the gas compound to be detected.

For example, in case the gas compound to be detected is $CO_2$, it is preferred that the extension of each element of the first device of the detector and the extension of the first elements of the emitter is 1.075 µm corresponding to an absorption wavelength of 4.3 µm for $CO_2$ being the gas compound to be detected, while the extension of each element of the first device of the detector and the extension of the first elements of the emitter is 0.975 µm corresponding to an absorption wavelength of 3.9 µm not being absorbed by $CO_2$ and as such being unaffected by the presence of $CO_2$ gas.

By means of such arrangement, a drift e.g. in the heater may be compensated given that such drift affects both the measurement channel and the reference channel. E.g. by subtracting a measurement result from the measurement channel from a measurement result from the reference channel, such drift can be eliminated by way of compensation. In addition, contamination effects can be compensated, as well as common-mode rejection of intensity noise of the source. This scheme may in a preferred embodiment be extended to multiple reference channels, each of the reference channels providing emissivity in a band outside the band of the gas component to be detected by the measurement channel. By such arrangement, active compensation of long-term drifts of the heater temperature can be achieved which e.g. is induced by degradation of the heater material by comparing a relative intensity of detected radiation between these multiple reference channels, and compensating the measurement result of the measurement channel dependent on such comparison.

In case the thermal sensors in the detector include thermocouples for both devices, signals supplied by the thermocouples (or thermopiles) may simply be subtracted from each other a result of which subtraction provides a measure of the concentration of the relevant gas compound. By means of the subtraction, an offset in the signal of each channel is eliminated that is induced by light that is not absorbed by the gas compound, such as $CO_2$, that is to be detected in case of a gas sensor. Small intensity fluctuations of the emitter may also be corrected for. In a preferred embodiment, a long-term drift of the emitter can be corrected by dividing the signals of the measurement channel and the reference channel. A combination of subtraction and division may be envisaged. Such signal processing may be implemented in a determination unit which may be embodied hardwired, or as software running on a controller.

In case both thermals sensor include bolometers, the determination unit preferably is configured to read signals supplied by the bolometers, which in this instance may be resistance values, and calculate a driftfree result of the gas concentration from the read signals, e.g. by means of subtraction or division.

The infrared based sensor preferably comprises a volume between the infrared emitter and the infrared detector for accepting a gas to be investigated as to the presence or absence and/or the concentration of a specific gas compound in that gas. Given that the concept of infrared based sensing includes the gas compound to absorb radiation of the band/wavelength the emitter and the detector are tuned to selectively emit/absorb, and specifically to build a relation between the radiant flux at this wavelength at the emitter and the radiant flux at this wavelength at the detector after travelling the volume, an amount of radiation absorbed by the gas compound present in the volume can be derived which is proportional to a concentration of this gas compound in the volume. Emitter and detector can be arranged in a common plane, e.g. on a common carrier, and may be arranged at different ends of the common carrier. A reflector may be provided in the infrared based sensor for deflecting the emitted radiation towards the detector.

It is preferred that the detector includes an encapsulation for sealing a volume at one or both sides of each of the substrate/membranes. In such embodiment, a window is provided in the encapsulation for allowing the configurations of the detector to be exposed to the infrared radiation, which window is coupled to the volume between the emitter and the detector. A window may also be provided in an encapsulation of an emitter which may prevent convection from ambient air to impact a temperature distribution on a membrane of the emitter.

Such gas sensor can be realized at chip scale, hence requiring a chip area of few $mm^2$, wherein commercial $CO_2$ sensors, for example, require a footprint on the order of several $cm^2$, which prohibits their deployment in applications where small sensor dimensions are important such as in mobile applications including mobile phones, tablets, etc.

Hence, in a preferred embodiment of the gas sensor, optical absorption of the measurand gas compound in the measurement volume results in intensity changes of infrared radiation of the subject band incident on the (photo-)detector. The measured infrared radiation is generated by the infrared emitter co-integrated in the system. The subject gas sensor preferably can be manufactured compatible to CMOS processing and hence is compatible with wafer-scale fabrication schemes hence enabling a straightforward and cost-effective extension of the present sensing approach to multiple wavelength windows, thus giving rise to multi-channel gas sensors. Therefore, in one embodiment of the infrared based sensor, more than two measurement channels are implemented, and preferably, in addition a single reference channel is implemented. The various measurement channels are designed to selective emissivity in the various bands the gas compounds to be detected show absorption. The reference channel preferably is designed to selective emissivity in a band none of the gas compounds to be detected shows absorption. The design of a channel including the corresponding infrared heater and the corresponding detector is performed by suitable shaping and dimensioning elements as introduced above. Preferably, the heater provides all sets of different elements on a common membrane or on microbridges spanning a common recess. In contrast, the detector may include a dedicated device/substrate per channel solely including the set of elements required for absorbing radiation in the assigned band.

Preferably, the underlying configurations represent optically effective components based on metamaterial absorber structures that allow for CMOS-compatible chip-scale integration. These materials are used both for the spectrally selective generation and detection of infrared light. The light source preferably is comprised of a MEMS heater patterned with a metamaterial configuration that tailors the emissivity and thereby the spectrum of thermally emitted light. Light detection follows a thermal scheme, e.g. a thermopile or a bolometer, with the metamaterial of the configuration of the detector providing strong absorption in the wavelength band of interest and near zero absorption outside this wavelength band.

A parameter additionally determining a magnitude of relative changes in the optical absorption as function of the measurand gas compound concentration—also referred to as absorption contrast—is the propagation length of probe light inside the gas volume. While conventionally it is aimed at maximizing this propagation length such effort not only increases a footprint of the infrared based sensor but also may require the introduction of costly light guiding schemes in order to ensure sufficient illumination of the detector. Instead, the present infrared based sensor relies on an efficient radiation transfer between emitter and detector, which e.g. is supported by means of an infrared emitter supplying higher power in the relevant band.

Preferably, the absorption wavelength is kept in a range that allows for chip-scale integration. This in turn allows for the use of both smaller emitter and detector dimensions compared to conventional sensors, while maintaining efficient radiation transfer. A possibly lower absorption contrast can be compensated by superior signal conditioning capabilities that a chip-scale-system, and in particular a CMOS-based system offers. Hence, it is preferred to integrate circuitry in the detector which circuitry is configured to filter the signals of the thermal sensor/s, amplify, and calibrate on-chip, thus limiting noise pick-up from the environment to a minimum. Such circuitry preferably is integrated into the substrate of the detector. In a different embodiment, emitter and detector are embodied on the same substrate, e.g. silicon substrate, and circuitry is integrated in this substrate and configured to control the heater to process the signals of the thermal sensor/s.

On the end of the infrared emitter, another advantage a miniaturized system based on micro-machined thermal sources offers over standard light sources such as incandescent bulbs is a substantially smaller time constant. In particular, this allows for the use of modulation schemes in which e.g. the emitter intensity is modulated and the electrical signal from the thermal sensor/s is constrained to a narrow bandwidth around the modulation frequency (lock-in scheme), thereby significantly reducing the influence of low-frequency noise.

Multi-channel sensors may be implemented by structuring the emitter surface with a periodic pattern which contains multiple geometries that give rise to multiple emission peaks at different wavelengths. Similarly, when deployed on a thermal infrared detector, metamaterials with different absorption resonances can give rise to spectrally selective detection.

Other advantageous embodiments of the gas sensor package are listed in the dependent claims as well as in the description below.

BRIEF DESCRIPTION OF THE DRAWINGS

Embodiments of the present invention, aspects and advantages will become apparent from the following detailed description thereof. Such description makes reference to the annexed drawings, wherein the figures show.

DETAILED DESCRIPTION OF THE DRAWINGS

Same elements are referred to by same reference numerals across all figures.

Figure 1:
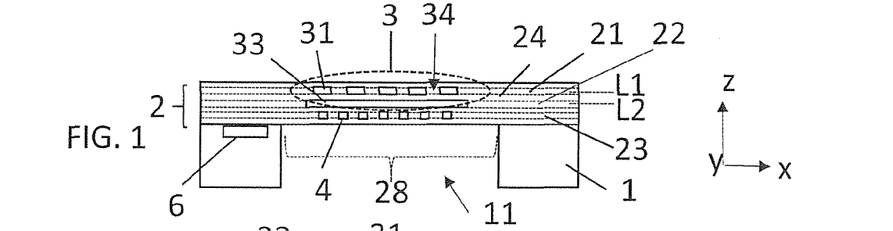
FIGS. 1 to 5 cuts of infrared devices according to embodiments of the present invention.

FIG. 1 illustrates a cut of an infrared device according to an embodiment of the present invention. The device comprises a substrate 1 and a stack of layers 2 arranged on the substrate 1. The substrate 1, which preferably is a semiconductor substrate, has a recess 11 through an entire thickness of the substrate 1, the recess 11 being made e.g. from etching or otherwise removing material from the substrate 1. The recess 11 evokes a membrane 28 made from the layer stack 2 spanning the recess 11 in the substrate 1. The layer stack 2 comprises multiple layers, preferably insulating and metal layers in an alternating fashion, of which layers only metal layers 21, 22 and 23 and insulating layer 24 between metal layers 21 and 22 are explicitly labelled.

The infrared device according to FIG. 1 may also be referred to as semiconductor chip comprising the bulk substrate 1, such as silicon bulk material, which is covered a CMOS layer stack 2 as defined in CMOS processing. The layer stack 2 preferably is structured for building a configuration 3—referred to by a dotted ellipse—arranged in the membrane 28. The configuration 3 comprises first elements 31—and presently no other elements—made from the metal layer 21 by conventional structuring. The electrically conducting elements 31 are arranged in a pattern in a first layer L1 of the membrane 28. Each first element 31 in the present example may take the shape of a stripe a length of which stripe can be seen in the present cut, however, other shapes may be implemented instead. The first elements 31 are arranged in a two-dimensional array in the first level L1 defined by the x- and y-axis, and in their entirety form a pattern. In the next lower metal layer 22, i.e. on level L2, a metallic film 33 is realized. Presently, the film 33 extends only across or within the membrane 28 in the x-y plane of the device. Otherwise a thermal short would be achieved to the substrate 1 thereby reducing the efficiency in case of an emitter, or the responsivity in case of a detector. Hence, the metal layer 22 may not be structured for implementing the film 33, but may represent the film 33 as such. A heater 4 is arranged in the next lower metal layer 23, e.g. in form of a resistive heater a few meandering lines of which are indicated in FIG. 1. The heater 4 is arranged for heating the configuration 3. Preferably, electronic circuitry (not shown) is integrated into the infrared device which circuitry may be connected to the heater 4 and be configured to control the heater 4, e.g. by switching a power switch on or off. Hence, the configuration 3 and the heater 4 are arranged in the membrane 28 above the recess 11. This arrangement is owed to reducing a heat transfer from the membrane 28 to the rest of the substrate 1. Levels L1 and L2 indicate planes of the configuration in which the pattern and the film 33 are arranged, which levels are in parallel to a plane extension of the membrane which plane extension presently is referred to as x/y extension.

Since the infrared device of FIG. 1 comprises a heater 4, the device is an infrared emitter. By switching on the heater 4 and applying heat to the configuration 3, the configuration 3 is triggered to selectively emit infrared radiation at the desired band only. A circuitry 6 may be integrated into the substrate 1, e.g. a silicon substrate, for controlling the heater 4 e.g. via a power switch also integrated into the device.

Figure 2:
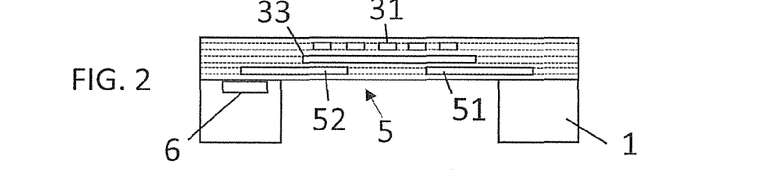

FIG. 2 illustrates a cut through another infrared device according to an embodiment of the present invention. It is assumed that this infrared device is exposed to infrared radiation incident from outside the device. Many elements are identical to the embodiment of FIG. 1 and are therefore not labelled again in view of enhancing illustration. The infrared device of FIG. 2 differs from the device of FIG. 1 in that it is an infrared detector instead of an infrared emitter. Therefore, instead of a heater 4, the infrared device of FIG. 2 comprises a thermal sensor 5 in form of one or more thermopiles, presently two thermopiles indicated by reference numerals 51 and 52. The thermopiles preferably are made from the metal layer 23. Each thermopile includes a multitude of thermocouples connected to each other at junctions. The junctions reside either on the membrane 28 or outside the membrane 28 on the substrate 1 such that a thermal difference can be detected, wherein the hot junctions of the thermopiles reside on the membrane 28 and are arranged to sense a temperature of the membrane 28 at these hot junctions which temperature is proportional to the radiation emitted by the configuration 3. Hence, the infrared radiation applied to and selectively absorbed by the configuration is converted into heat which heat is sensed by the thermal sensor 5. A circuitry 6 may be integrated into the substrate 1, e.g. a silicon substrate, serving as determination unit for evaluating signals provided by the thermal sensor 5.

Figure 3:
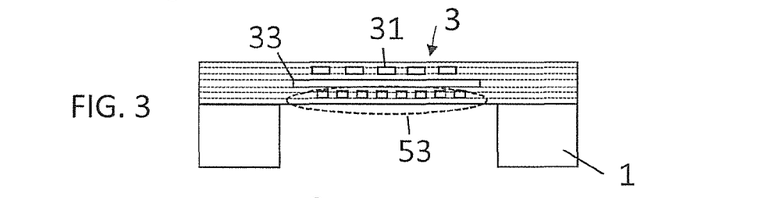
Figure 4:
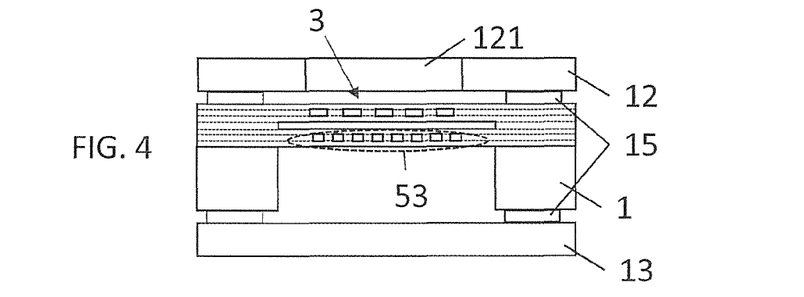
Figure 5:
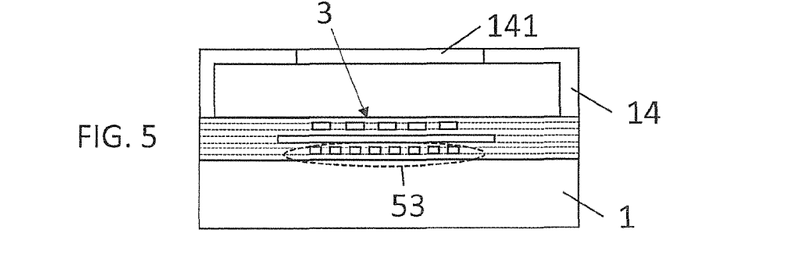

FIG. 3 illustrates another cut through an infrared device according to an embodiment of the present invention. The infrared device of FIG. 3 again is an infrared detector instead of an infrared emitter, which infrared detector of FIG. 3 differs from the detector of FIG. 2 in that instead of thermopiles 51, 52 a bolometer is used as thermal sensor. The bolometer presently comprises a resistive temperature sensor 53 made from conductive structures, such as metal wires, arranged in the membrane 28, and preferably structured from one of the conductive layers of the stack, preferably a layer underneath the layers contributing to the configuration 3. In combination with the configuration 3, and supported by a good thermal isolation provided by the membrane 28, the resistive temperature sensor 53 builds the bolometer. FIGS. 4 and 5 show different embodiments of infrared detectors using a bolometer as thermal sensors, again in side cuts. The detector of FIG. 4 differs from the detector of FIG. 3 in that a volume on both sides of the membrane 28 is limited by an encapsulation. The encapsulation is made from two substrates 12 and 13, e.g. silicon substrates, bonded to the stack of layers 2 or to the substrate 1 by suitable means, e.g. by an adhesive 15. The volume in the encapsulation may be evacuated or may be filled with a protection gas in order to enhance infrared transmission.

A different variant of encapsulation is shown in FIG. 5. A single cap 14 is used as encapsulation, which cap preferably is attached to the layer stack 2, e.g. by bonding. In the present example, the substrate 11 does not have a recess 11 such that there is no backside of a membrane to be evacuated.

In both embodiments of FIG. 4 and FIG. 5, infrared radiation from a measurement volume outside the device is desired to meet the configuration 3 of the device such that a window 121 and 141 respectively is arranged in the encapsulation 12 or 14 respectively, which window preferably is transmissive in the infrared spectrum, at least in the desired band. The window is integrated in the encapsulation 12 and 14 respectively and preferably faces the configuration 3.

Figure 6:
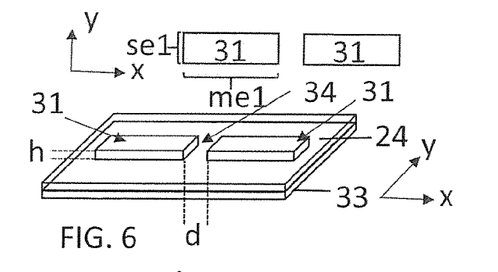
FIG. 6 a top and a perspective view on a configuration as used in an embodiment of the present invention.

FIG. 6 illustrates a top view and a perspective view (below the top view) of two first elements 31 of a configuration 3 as used in an embodiment of the present invention. The first elements 31 are two out of a set of first elements possibly containing many more than two first elements 31. Each first element 31 has the shape of a rectangle stripe with a length me1 and a width se1. In the present planar x-y-system, the length me1 of the stripe which is also referred to as main extension me1 of the first element 31 coincides with the x-axis while the width se1 of the stripe which is also referred to as subordinate extension se1 of the element 31 coincides with the y-axis orthogonal to the x-axis. Preferably, the main extension me1 exceeds the subordinate extension se1, and preferably exceeds by far, e.g. more than three times, more than five times, or more than ten times. In view of the magnetic polariton desired to be induced into the configuration 3 by means of infrared radiation, the main extension me1 is dimensioned in relation to a band in the infrared spectrum to be selectively be emitted. Preferably, the main extension me1 is a quarter of a wavelength λ representing the desired band, e.g. a center of the band. The subordinate extension se1 may also induce an infrared resonance in the configuration 3 at a wavelength defined by the subordinate extension. However, such wavelength may not be of interest. The first elements 31 are not connected to each other.

The first elements 31 reside on an insulating layer 24 which in turn is deposited on a continuous metal film 33. None of the elements 31 is electrically connected to the film 33. A height h of each first element 31 is in the range of 100 nm. A vertical distance d between the first elements 31 and the film 33—which represents a thickness of the insulating layer 24—is around by 100 nm. A gap 34 between two neighboring first elements 31 in the first level L1 has a distance d that may also be in the range of 100 nm. It was found that the distance d may not be of utter importance to the resonance characteristic desired to be evoked.

Figure 7:
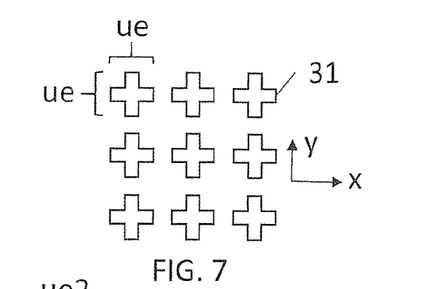
FIG. 7 a top view on another configuration as used in an embodiment of the present invention.

FIG. 7 illustrates a top view only on a configuration as used in an infrared device according to an embodiment of the present invention. The configuration comprises multiple first elements 31, each of which first elements 31 takes the shape of a cross. Presently, the main extensions of the crosses are equal along each of the axis x and y such that it is legitimate to refer to such extension as a uniform extension ue, at least along the axis orthogonal to each other. Hence, the two legs of each cross are uniformly dimensioned dependent the desired wavelength to be emitted by the configuration 3.

FIGS. 8 to 11 each illustrates a top view on configurations applied in a gas sensor according to an embodiment of the present invention. The associate configuration of a corresponding infrared emitter 7 is shown on the very left, while the configurations of the detector 8 are shown on the right hand side. The detector 8 preferably comprises two infrared devices 81 and 82 for detecting infrared radiation at two different wavelengths.

For all embodiments in these FIGS. 8 to 11, the infrared emitter 7 has a pattern including, and preferably consisting of two different elements, i.e. at least one first element 31 and at least one second element 32. The first and second elements 31 and 32 are preferably arranged on a common membrane or at least arranged over a common recess in a substrate. Instead, the configurations of the detector 8 preferably are arranged on different substrates. The substrates contributing to the detector 8 may or may not have a membrane.

On the detector-side, the first elements 31 are exclusively grouped in the configuration of the first device 81 without any second element 32 being present therein. The second elements 32 are exclusively grouped in the configuration of the second device 81 without any first element 31 being present therein. Hence, the first device 81 is reserved for absorbing infrared radiation in a first band which infrared radiation preferably is shaped and emitted via the configuration including the first elements 31 in the emitter 7, while the second device 82 is reserved for absorbing infrared radiation in a different band which infrared radiation is shaped and emitted via the second elements 32 in the emitter 7. Hence, it is preferred that the shapes and the dimensions of the first elements 31 in the emitter 7 and in the first device 81 of the detector 8 are identical, and that the shapes and the dimensions of the second elements 31 in the emitter 7 and in the second device 82 of the detector 8 are identical. Each first element 31 has the shape of a cross, and each second element 32 has the shape of a cross as well, however of a different size. A uniform extension ue2 of the crosses serving as second elements 32 is smaller than a uniform extension ue1 of the crosses serving as first elements 31.

Figure 8:
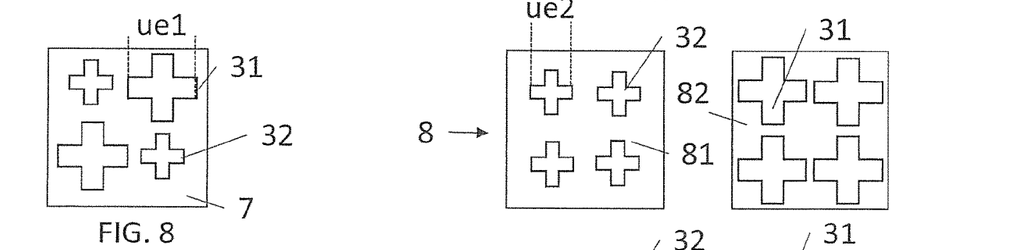
FIGS. 8 to 11 top views on configurations of infrared based sensors according to embodiments of the present invention.

Hence, by heating the configuration of the emitter 7 of FIG. 8, infrared radiation limited to two different bands is emitted and may be applied to a gas in a common volume between the emitter 7 and the corresponding detector 8. In the detector 8, the infrared radiation of the specific band is absorbed by the configurations 81 and 82.

Generally, and applicable to all embodiments of FIGS. 8 to 11, the number of first and second elements 31 and 32 may exceed the number shown by far. The number may depend on an overall target size of the corresponding chip. The number of elements of the same kind (first, second) may vary between the emitter 7 and the detector 8, but preferably is the same. A heater is not shown for each emitter 7 although being present for heating the configuration of the emitter 7. Each device 81, 82 of the detector 8 preferably has its own thermal sensor (not shown) in form of either a thermopile of a bolometer.

Figure 9:
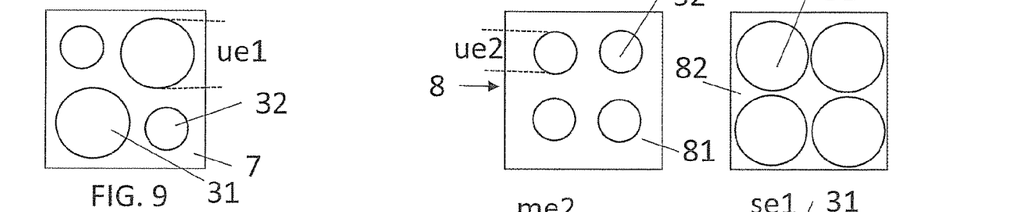

The configurations of FIG. 9 differ from the ones shown in FIG. 8 in that circles are used as first and second elements 31 and 32 instead of crosses. The uniform extensions ue1 and ue2, which are the diameters of the first and second elements 31 and 32 are dimensioned dependent on the wavelength of infrared radiation to be emitted or absorbed by the configurations.

Figure 10:
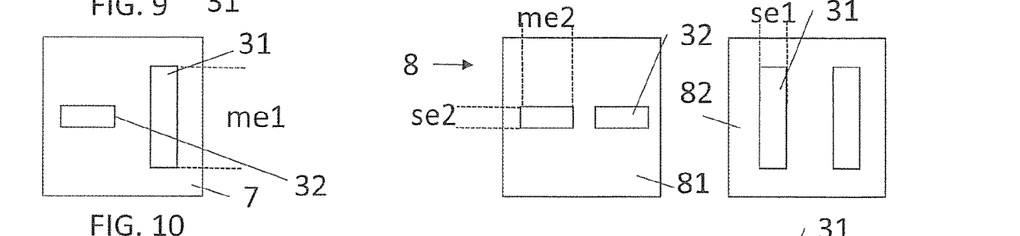

In the configurations shown in FIG. 10, elements are provided that do not show uniform extension but clearly have a main extension and a subordinate extension. Presently, the first and second elements 31 and 32 are both stripes/rectangles with a main extension me1, me2 each which the subordinate extension se1, se2 orthogonal to the main extension by far. The main extensions me1, me2 of the first and the second elements 31 and 32 are dimensioned to emit or absorb infrared radiation in two different bands, while the subordinate extensions do not impact the measurement.

Figure 11:
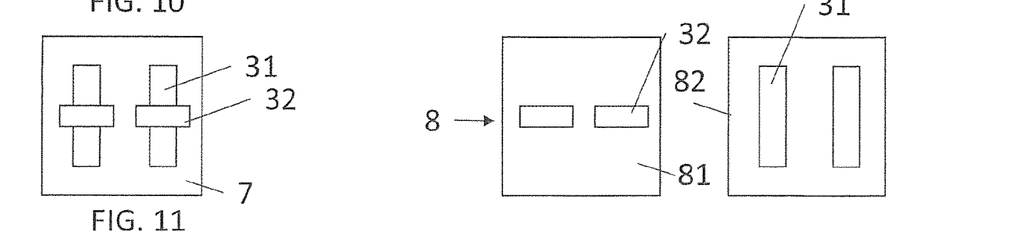

In addition, the first elements 31 and the second elements 32 differ in orientation in both the emitter 7 and the detector 8. The first elements 31 are arranged with their main extension me1 orthogonal to the main extension me2 of the second elements 32. Compared to the configurations of FIGS. 8 and 9, such arrangement and orientation improves a detection of the corresponding bands by exploiting polarization. In particular, when the two bands are close to each other, the signals stemming from each of the measurement channel and the second measurement channel or reference channel according to FIG. 9 or 10 may be impacted by crosstalk. In the embodiments of FIGS. 10 and 11 instead, the orientation of the first elements 31 in the detector 8 and the orientation of the second elements 32 in the detector 8 (orthogonal to each other) provide for an additional separation of the channels by polarization thereby avoiding crosstalk.

The configurations of the infrared based sensor of FIG. 11 differs from the one in FIG. 10 in that in the emitter 7 each first element 31 is connected to a different one of the second elements 32. Hence, first and second elements 31 and 32 are connected pairwise, such that each pair forms a cross with different lengths of its legs. Such arrangement in the emitter 7 saves area on the substrate. Instead, in the detector 8 the first and second elements 32 and 31 preferably remain separated from each other as in FIG. 10 given that each device 81 and 82 requires an individual thermal sensor.

Figure 12:
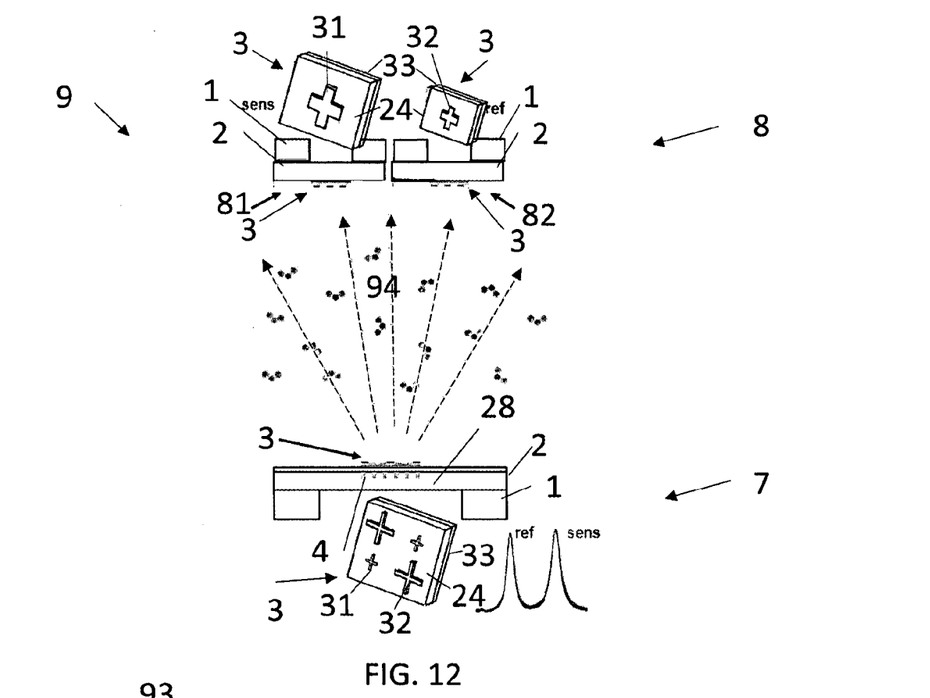
FIG. 12 a schematic infrared based sensor according to an embodiment of the present invention.

FIG. 12 shows a schematic infrared based sensor according to an embodiment of the present invention. Encapsulation, housing etc. are omitted for illustration purposes. The infrared emitter 7 is of a design similar to the emitter of FIG. 1, except that the configuration 3 is arranged on top of the membrane 28 instead of residing in the membrane 28. The heater 4 remains integrated in the membrane 28. The substrate 1 supports the layer stack 2 from which the membrane 28 is built. A detailed view of the emitter 7 introduces the configuration 3, which again is different from the embodiment of FIG. 1, comprising a metallic film 33, a dielectric layer 24, a set of first elements 31 and a set of second elements 32 arranged on the dielectric layer 24. The first and second elements 31 all have the shape of a cross, wherein the first elements 31 have a first uniform extension ue1 and the second elements 32 have a second uniform extension ue2 different from the first uniform extension. As a result, the infrared emitter 7 is designed and configured to emit infrared radiation at two different frequency bands. This filtered radiation is emitted into a volume 94 filled by a gas to be investigated. Gas compounds as schematically indicated in the volume 94 absorb the infrared radiation of the one band while do not absorb the radiation of the other band.

An infrared detector 8 comprises two infrared devices 81 and 82 for absorbing any incident radiation in the same two bands. Each device 81, 82 of the detector 8 comprises a substrate 1 separate from each other, including a recess contributing to a membrane. On top of each substrate 1, a configuration 3 is arranged which is shown in more detail in the expanded view. While the first device 81 comprises a configuration 3 comprising the first elements 31 only, the configuration 3 of the second device 32 comprises the second elements 32 only. Both configurations 3 include a metallic film 33 and a dielectric layer 24 between the elements 31, 32 and the film 33. Each device 81, 82 comprises a thermal sensor not shown. Hence, the first device 81 solely absorbs infrared radiation in the first band, while the second device only absorbs infrared radiation in the second band. The emission and detection of infrared radiation of the second band is also referred to as reference channel while the emission and detection of infrared radiation in the first band is referred to as measurement channel, given that the results of the two channels can be combined in order to eliminate a drift component from the overall measurement result.

During operation the emitter 7 emits infrared radiation limited to the two bands in response to activating the heater 4. The first band is selected according to an absorbance characteristic of the gas compound to be detected. The second band is selected such that the gas compound does not absorb radiation in that band. In the volume 94, which presently is supposed to contain gas including the gas compound desired to be detected, the infrared radiation of the first band is absorbed by this very gas compound during its path from the emitter to the detector 8, possibly via a reflector. Given that the amount of radiation emitted in the subject band is known, a concentration of the gas component in the gas in volume 94 can be derived from this amount and from the amount of radiation detected in the detector 8 for the subject band.

Figure 13:
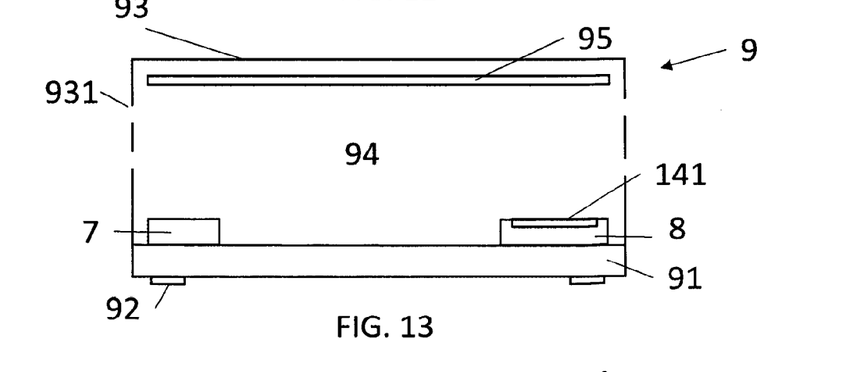
FIG. 13 a cut through an infrared based sensor according to an embodiment of the present invention.

FIG. 13 illustrates a schematic cut through an infrared based sensor according to an embodiment of the present invention. The infrared based sensor 9 comprises a carrier 91, e.g. a leadframe, a PCB or another carrier supporting an infrared emitter 7 and an infrared detector 8. Both, emitter 7 and detector 8 may be for example, of the kind introduced in FIG. 12 and hence be prepared for emitting and absorbing infrared radiation in two different bands. In one embodiment, the detector 8 may include bolometers as thermal sensors one of each assigned to the two infrared devices included in the detector 8. The detector 8 may include a window 141 for allowing transmission of the infrared radiation onto the configurations of the detector 8.

The carrier 91 may include conducting paths (not shown), and provide contact pads 92 for electrically connecting the sensor 9 to the outside world. The infrared based sensor 9 further includes a housing 93 defining a volume 94 in the housing 93 to be filled with gas to be investigated. For this purpose, the housing 93 may include one or more openings 931 such that gas to be investigated can enter and leave the housing 93. In addition, a reflector 95 may be arranged in the housing 93 for reflecting infrared radiation emitted by the emitter 7 and redirecting such radiation to the detector 8.

The operation of the infrared based sensor 9 of FIG. 13 may be identical to the operation disclosed in connection with the embodiment illustrated in FIG. 12.

Figure 14:
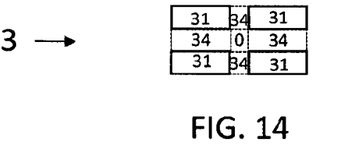
FIG. 14 to FIG. 17 top views on configurations as used in embodiments of the present invention.
Figure 15:
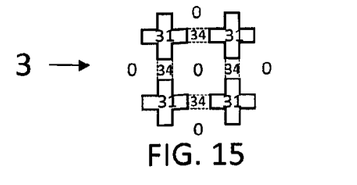

While it is preferred, that the film of a configuration extends continuously underneath each the entire pattern and any gaps between elements contributing to the pattern, the embodiments of FIGS. 14 to 17 illustrate different shapes of a metal film that may be used instead of a continuous film. Here, it is preferred that the film at least covers an area in the second level that is defined by a projection of the first elements 31 on the first level and gaps 34 between neighboring first elements 31 towards the second level. In all the examples shown, the film covers an area defined by the extensions of the first elements 31 and the gaps 34 but do not cover area labelled by "0". In FIG. 14 first elements 31 take the shape of stripes, and the shape of crosses in FIG. 15. The first elements 31 are disconnected from each other by means of gaps 34. As can be derived from FIGS. 14 and 15 and generally applicable in the context of the present invention when referring to separate, individual first or second elements 31 or 32, a gap 34 between two neighboring elements shall at least include a shortest path between these neighboring elements. Given that neighboring elements may have parallel edges facing each other, an area between these parallel edges is considered as gap 34, such as indicated in FIG. 14. Instead an area labelled "0" in the present Figures does not represent a gap between two neighboring elements given that only elements are considered as neighboring elements that have a distance between each other that is closer than to any other element. In the example of FIG. 15, for example, only the area between the legs of two neighboring first elements 31 facing each other is considered as gap 34. Hence, the area/s labelled by "0" may be excluded from the film 33.

Figure 16:
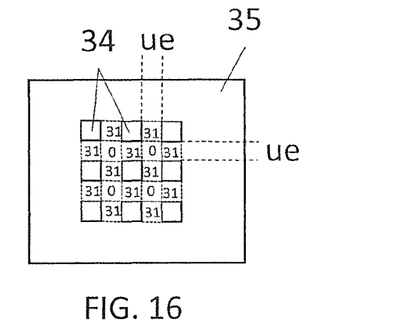

In the pattern of FIG. 16, the first level containing the set of elements is a continuous metallic layer 35 with holes etched, stamped or otherwise manufactured into the layer 35. The holes have square shape but may have a different shape such as circles, and presently are arranged at equal distances ue1 from each other. In this example, the holes represent gaps 34 between two neighboring elements 31. An element 31 is defined at extension between two neighboring gaps 34. Such virtual elements 31 are illustrated by dotted lines in the example of FIG. 16. Here the elements 31 are connected to each other. The distance ue1 between two gaps 34 represents the uniform extension ue1 of a first element 31 that is to be dimensioned for emitting infrared radiation in the desired band. Presently there is only a uniform extension ue1 defined between any two gaps 34. A film 33 for the present pattern to be arranged in the second level presently is preferred to have the same extension as the metallic layer 35 except for areas labelled "0".

Figure 17:
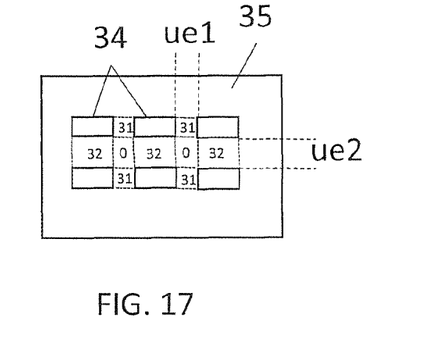

In the example of FIG. 17, instead, the vertical spacing between two adjacent gaps 34 is large and denotes a second uniform extension ue2 of a second element 32, which is different from a uniform extension ue1 of a first element 31 represented by the horizontal spacing between two adjacent gaps 34.

While above there are shown and described embodiments of the invention, it is to be understood that the invention is not limited thereto but may be otherwise variously embodied and practiced within the scope of the following claims.

The invention claimed is:
1. Infrared device, comprising
   a substrate, a recess in the substrate,
   a membrane spanning at least a portion of the recess, and supported by the substrate:
   a configuration for one of selectively emitting and selectively absorbing infrared radiation of a band, the configuration being arranged on or in the membrane and comprising: a pattern made from an electrically conducting material on a first level; an electrically conducting film on a second level; and a dielectric layer between the pattern and the film; and one or more components, the latter comprising one or more of a heater arranged for heating the configuration to emit the infrared radiation of the band, and a thermal sensor arranged for sensing the selective infrared radiation of the band absorbed by the configuration, wherein said components are arranged on or in the membrane, so as to be electrically insulated from each of the pattern made from said electrically conducting material on the first level and the electrically conducting film on the second level, and the film at least extends over an area of the second level that is defined by a projection of the pattern and gaps in the pattern onto the second level, and a thickness of the dielectric layer between the pattern and the film is less than a center wavelength of the band.

2. The infrared device according to claim 1, wherein said configuration with said components form part of a CMOS-compatible layer stack that is supported by the substrate.

3. The infrared device according to claim 1, wherein the membrane has a shape of a bridge bridging the recess and is configured to allow gas to be exchanged between the recess and a volume outside the membrane.

4. The infrared device according to claim 1, wherein said pattern comprises a set of first elements and gaps.

5. The infrared device according to claim 4, wherein said first elements are disconnected from each other by said gaps.

6. The infrared device according to claim 4, wherein
the configuration further comprises, on said first level, a layer that comprises holes acting as said gaps, and
each of said first elements is formed by a portion of the layer between two neighboring gaps of said gaps, so as to form said pattern.

7. The infrared device according to claim 4, wherein an extension of each of said first elements in the first level is dimensioned dependent on the band of infrared radiation to be emitted or absorbed by the configuration.

8. The infrared device according to claim 7, wherein the extension of each said first elements is dimensioned according to a wavelength λ representing a center of the band divided by four.

9. The infrared device according to claim 7, wherein:
said extension is a main extension of each of said first elements along a first axis in the first level, and
an extension of each of said first elements along a second axis in the first level orthogonal to the first axis is at least three times less than said main extension.

10. Infrared emitter, comprising an infrared device according to claim 1, which infrared device includes the heater as part of said components.

11. Infrared detector, comprising an infrared device according to claim 1, which infrared device includes the thermal sensor as part of said components.

12. Infrared detector according to claim 11, wherein the thermal sensor comprises at least one thermocouple extending from the membrane to the substrate.

13. Infrared detector for detecting infrared radiation at two different bands, comprising a first infrared device according to claim 1, which first infrared device includes a first thermal sensor as part of said components of the first infrared device, a second infrared device according to claim 1, which second infrared device includes a second thermal sensor as part of said components of the second infrared devices, wherein
the configuration of the second infrared device is adapted to selectively absorb infrared radiation of a band that differs from the band of the first infrared device.

14. Infrared detector according to claim 13, wherein
the pattern of the first device comprises a set of first elements,
the pattern of the second device comprises a set of second elements,
an extension of each of said first elements is dimensioned dependent on the band of infrared radiation to be selectively absorbed by the configuration of the first infrared device, and
an extension of each of said second elements is dimensioned dependent on the other band of infrared radiation to be selectively absorbed by the configuration of the second infrared device.

15. The infrared detector according to claim 14, wherein
the extension of each of said first elements is a main extension thereof along a first axis in the first level,
an extension of each of said first elements along a second axis in the first level orthogonal to the first axis is at least three times less than the main extension thereof,
the extension of each of said second elements is a main extension thereof along the second axis, and
an extension of each of the second elements along the first axis is at least three times less than the main extension thereof.

16. The infrared detector according to claim 14, wherein
the extension of each of said first elements is a uniform extension along a first axis in the first level and along a second axis orthogonal to the first axis, and
the extension of each of the second elements is a uniform extension along the first axis and along the second axis.

17. The infrared detector according to claim 13, wherein the substrate of the first infrared device and the substrate of the second infrared device are separate from each other.

18. The infrared detector according to claim 13, wherein the substrate of the first infrared device and the substrate of the second infrared device are a common substrate.

19. The infrared device according to claim 1, wherein said configuration is designed as a metamaterial perfect absorber.

20. Infrared based sensor, comprising
an infrared device according to claim 1, configured as an infrared emitter, whereby the configuration of the emitter is designed as a metamaterial perfect absorber for selectively emitting infrared radiation in a band defined by an absorption wavelength for a gas compound to be detected, and the emitter comprises said heater, as part of said components of the infrared emitter, for heating said configuration,
an infrared device according to claim 1, configured as an infrared detector, whereby the configuration of the emitter is designed as a metamaterial perfect absorber for selectively absorbing infrared radiation in the band that is selectively emitted by the infrared emitter, in operation, and the detector comprises a thermal sensor, as part of said components of the infrared detector, for sensing the infrared radiation selectively absorbed by the metamaterial perfect absorber of the detector and supplying a corresponding electrical signal, in operation,
a volume between the infrared emitter and the infrared detector, which volume can be filled with a gas, in operation, and
a determination unit, configured to determine a concentration of the gas compound in the gas filling the volume dependent on the electrical signal supplied by the thermal sensor.

* * * * *